US009134302B2

(12) United States Patent
Pergolizzi et al.

(10) Patent No.: US 9,134,302 B2
(45) Date of Patent: *Sep. 15, 2015

(54) ANALYTE DETECTION UTILIZING POLYNUCLEOTIDE SEQUENCES, COMPOSITION, PROCESS AND KIT (75) Inventors: Robert G. Pergolizzi, New Milford, NJ (US); Jannis G. Stavrianopoulos, New York, NY (US); Elazar Rabbani, New York, NY (US); Dean L. Engelhardt, New York, NY (US); Stan Kline, Brooklyn, NY (US); Paula J. Olsiewski, New York, NY (US)

(73) Assignee: Enzo Diagnostics, Inc., Syosset, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/479,995

(22) Filed: Jun. 7, 1995

(65) Prior Publication Data
US 2010/0273145 A1 Oct. 28, 2010

Related U.S. Application Data (60) Continuation of application No. 08/342,667, filed on Nov. 21, 1994, now abandoned, which is a continuation of application No. 07/805,274, filed on Dec. 10, 1991, now abandoned, which is a division of application No. 07/607,787, filed on Oct. 26, 1990, now abandoned, which is a continuation of application No. 06/922,757, filed on Oct. 24, 1986, now abandoned, which is a continuation of application No. 06/491,929, filed on May 5, 1983, now abandoned.

(51) Int. Cl.
*C07H 21/00* (2006.01)
*G01N 33/53* (2006.01)
*C12Q 1/68* (2006.01)

(52) U.S. Cl.
CPC .............. *G01N 33/53* (2013.01); *C12Q 1/6813* (2013.01); *C12Q 1/6876* (2013.01)

(58) Field of Classification Search
CPC ..... G01N 33/53; C12Q 1/6876; C12Q 1/6813
USPC ......... 435/5, 6, 810; 436/501; 536/23.1, 22.5, 536/24.5, 24.3–24.33; 935/77, 78
See application file for complete search history.

(56) References Cited

U.S. PATENT DOCUMENTS

| | | | |
|---|---|---|---|
| 3,755,086 A | 8/1973 | Heimer | 195/103.5 R |
| 3,798,131 A | 3/1974 | Rounds et al. | 195/103.5 R |
| 4,302,204 A | 11/1981 | Wahl et al. | 435/172 |
| 4,358,535 A | 11/1982 | Falkow et al. | 435/5 |
| 4,366,241 A | 12/1982 | Tom et al. | 435/7 |
| 4,486,539 A | 12/1984 | Ranki et al. | 436/504 |
| 4,556,643 A | 12/1985 | Paau et al. | 436/501 |
| 4,581,333 A | 4/1986 | Kourilsky et al. | 435/6 |
| 4,711,955 A | 12/1987 | Ward et al. | 536/29 |
| 5,241,060 A | 8/1993 | Engelhardt et al. | 536/27 |
| 5,260,433 A | 11/1993 | Engelhardt et al. | 536/23.1 |

FOREIGN PATENT DOCUMENTS

| | | |
|---|---|---|
| EP | 70685 | 1/1983 |
| EP | 70687 | 1/1983 |
| EP | 0079139 B1 | 5/1983 |
| EP | 0097373 | 1/1984 |
| EP | 124221 | 11/1984 |
| EP | 0124221 A1 | 11/1984 |
| GB | 2019408 | 10/1979 |
| WO | 8301459 | 4/1983 |

OTHER PUBLICATIONS

Maniatis et al. [Molecular Cloning, Published by Cold Spring Harbor Laboratory, Cold Spring Harbor, New York, New York (1982)], pp. 51-54.*
Langer et al. [Proceedings of the National Academy of Sciences, USA, vol. 78, No. 11, pp. 6633-6637 (9181).*
Chard, T., *An Introduction to Radioimmunoassay and Related Techniques*, 3rd Revised Edition, pp. 161-162, 175, Elsevier Science Publishing, B.V., Amsterdam, N.Y. (1987).
Schuurs, A.H. et al., "Enzyme-Immunoassay," *Clinica Chimica Acta*, 81:1-40 (1977).
Bauman, J.G.J. et al., "Rapid and High Resolution Detection of in situ Hybridisation to Polytene Chromosomes Using Fluorochrome-labeled RNA," *Chromosoma*, 84:1-18 (1981).
Rudkin et al., "High Resolution Detection of DNA-RNA Hybrids in situ by Indirect Immuofluorescence," *Nature*, 265:472-473 (1977).
Manning, J. et al., "A Method for Gene Enrichment Based on the Avidin-Biotin Interaction. Application to the Drosophila Ribosomal RNA Genes," *Biochemistry*, 16:1364-1370 (1977).
Broker, T.R. et al., "Electron Microscope Visualization of tRNA Genes With Ferritin-Avidin: Biotin Labels," *Nucleic Acids Research* 5:363-384 (1978).
Sodja, A. et al., "Gene Mapping and Gene Enrichment by the Avidin-Biotin Interaction: Use of Cytochrome-C as a Polyamine Bridge," *Nucleic Acids Research*, 5:385-401 (1978).
Shapiro, R. et al., "The Reaction of Guanine Derivatives with 1,2-Dicarbonyl Compounds," *Biochemistry*, 5:2799-2807 (1966).
Litt, M., "Structural Studies on Transfer Ribonucleic Acid. I. Labeling of Exposed Guanine Sites in Yeast Phenylalanine Transfer Ribonucleic Acid with Kethoxal," *Biochemistry*, 8:3249-3253 (1969).

(Continued)

*Primary Examiner* — John S Brusca
(74) *Attorney, Agent, or Firm* — Anna DiGabriele Petti (57) ABSTRACT

A method of detecting in a sample an analyte (A) having a molecularly recognizable portion thereon, which comprises: providing (B) a molecular bridging entity having thereon: (i) a portion capable of recognizing the molecularly recognizable portion on the analyte; and (ii) a portion comprising a polynucleotide sequence; and (C) a signalling entity having thereon: (i) a polynucleotide portion capable of annealing to the polynucleotide portion of the bridging entity, thereby to form a stable polynucleotide hybrid, and (ii) a signal generating portion; forming a complex comprising: (1) the analyte (A) complexed through its molecularly recognizable portion to (2) the recognizing portion of the entity (B); the entity (B) being complexed through the polynucleotide portion thereon to (3) the polynucleotide portion of the signalling entity; and detecting a signal by means of the signal generating portion present in the complex.

8 Claims, 2 Drawing Sheets

(56) References Cited

OTHER PUBLICATIONS

Politz, S.M. et al., "Ribonucleic Acid-Protein Cross-Linking in *Escherichia coli* Ribosomes: (4-Azidophenyl) glyoxal, a Novel Heterobifunctional Reagent," *Biochemistry*, 20:372-378 (1981).
van Wezenbeek, P., "Nucleotide Sequence of the Filamentous Bacteriophage M13 DNA Genome: Comparison with Bacteriophage fd," *Gene*, 11:129-148 (1980).
Manning et al., "A New Method of in situ Hybridization," *Chromosoma*, 53:107-117 (1975).
Langer, P.R., "Enzymatic Synthesis of Biotin-labeled Polynucleotides: Novel Nucleic Acid Affinity Probes," *Proceedings of the National Academy of Sciences of the United States of America*, 78:6633-6637 (1981).
Halloran, M.K., "The Preparation of Nucleotide-protein Conjugates: Carbodiimides as Coupling Agents," *The Journal of Immunology.*, vol. 96, No. 3:373-378 (1966).
Brutlag, D., et al., "Properties of Formaldehyde-Treated Nucleohistone," *Biochemistry*, 8:3214-3218 (1969).
Jones, A.S. et al., "Bromination of Nucleic Acids and Their Derivatives," *Nature*, 183:1603-1605 (1959).
Lowe, C.R., "The Synthesis of Several 8-substituted Derivatives of Adenosine 5-monophosphate to Study the Effect of the Nature of the Spacer Arm in Affinity Chromatography," *European Journal of Biochem*, 73:265-274 (1977).
Dale, R.M.K. et al., "The Synthesis and Enzymatic Polymerization of Nucleotides Containing Mercury: Potential Tools for Nucleic Acid Sequencing and Structural Analysis," *Proceedings of the National Academy of Sciences of the United States of America*, 70:2236-2242 (1973).
Dale, R.M.K. et al., "Conversion of Covalently Mercurated Nucleic Acids to Tritiated and Halogenated Derivatives," *Nucleic Acids Research*. 2:915-929 (1975).
Cramer et al., "Eine Synthese der 6-Desoxy-6-amino-glucose," *Chem. Ber.* 92:384-391 (1959).
Roychoudhury, R. and Wu, R., "Terminal Transferase-Catalyzed Addition of Nucleotides to the 3' Termini of DNA," *Methods in Enzymology, LXV*, 43 (1980).
Rigby et al., "Labeling Deoxyribonucleic Acid to High Specific Activity in vitro by Nick Translation with DNA Polymerase I," *Journal of Molecular Biology*, 113:237-251 (1977).
H. Kossel, "Reaktion von Mononucleotiden mit Diazoniumsalzen," *2 Physiol. Chem.* 340, 210 (1965).
E.N. Moudrianakis et al., "Determination of Base Sequence in Nucleic Acids with the Electron Microscope, The Reaction of a Guanine-selective Marker with the Mononucleotides," *Biochim. Biophys. Acta*, 95:23-29, (1966).
Alwine, J.C. et al., "Detection of Specific RNAs or Specific Fragments of DNA by Fractionation in Gels and Transfer to Diazobenzyloxymethyl Paper," *Methods in Enzymology*, 68:220-242 (1979).
Barrio, J.R. et al., "Fluorescent Adenosine and Cytidine Derivatives," *Biochemical and Biophysical Research Communications*, 45:597-604 (1972).
Sattsangi, P.D. et al., "1,$N^2$-Ethenoguanine and $N^2$3-Ethenoguanine Synthesis and Comparison of the Electronic Spectral Properties of These Linear and Angular Triheterocycles Related to the Y Bases," *Journal of Organic Chemistry*, 42:3292-3296 (1977).
Yamasaki H. et al., "Effect of N-2-Acetylaminofluorene Modification on the Structure and Template Activity of DNA and Reconstituted Chromatin," *Cancer Research* 37:684-691 (1977).
Hoffman, K. et al., "Iminobiotin Affinity Columns and Their Application to Retrieval of Streptavidin," *Proceedings of the National Academy of Sciences of the United States of America*, 77:4666-4668 (1980).

Rigby, P.W.J. et al., "Labeling Deoxyribonucleic Acid to High Specific Activity in vitro by Nick Translation with DNA Polymerase I," *Journal of Molecular Biology*, 113:237-251 (1977).
Rudkin, G.T. et al., "High Resolution Detection of DNA-RNA Hybrids in situ by Indirect Immunofluorescence," *Nature*, 25:472-473 (1977).
Dunn et al., "Mapping Viral mRNAs by Sandwich Hybridization," *Methods in Enzymology, vol. 65, Part I, Nucleic Acids*, pp. 468-479 (Grossman, Edu), Academic Press, New York 1980.
Hu et al., "The making of strand-specific M13 probes," *Gene* 17:271-277 (1982).
Helling and Lomax, "The Molecular Cloning of Genes—General Procedures," Chapter 1, *Genetic Engineering*, Amanda Chakrabarty (editor), CRC Press, Boca Raton, Florida, 1978, pp. 1-30.
D. Horton, *Organic Synthesis*, John. Wiley & Sons Inc., New York, vol. 46. 1966, p. 1.
Dunn et al., "Mapping Viral mRNAs by Sandwich Hybridization," *Chemical Abstracts*, vol. 93, No. 7, Aug. 18, 1980, p. 437, Abstract No. 65229w.
Dunn et al., "Mapping Viral mRNAs by Sandwich Hybridization," *Methods in Enzymology, vol. 65, Part I, Nucleic Acids*, pp. 468-479 (Grossman, Edu.), Academic Press, New York 1980.
Hu et al., "The making of strand-specific M13 probes" *Gene* 17:271-277 (1982).
Sugiura et al., "Methods for enzymatic labeling of nucleic acids and polynucleotides," *Chemical Abstracts*, vol. 91, No. 23, Dec. 3, 1979, p. 219, Abstract No. 188423w.
Chard, T., "An Introduction to Radioimmunoassay and Related Techniques," *North Holland Publishing Company*, Amsterdam, NY Oxford (1978), pp. 1-29.
Tereba et al., *PNAS (USA)* 76:6486-90 (1979).
Drlica, *Understanding DNA and Gene Cloning*, John Wiley & Sons, Inc., NY (1984), p. 21.
Symons, *Nucleic Acid Probes*, CRC Press, Inc., Boca Raton, FL, 1989, pp. 130-131 and 36-38.
Keller et al., *DNA Probes*. Stockton Press, New York, NY, 1989, pp. 198-201.
Piper et al., *Nucleic Acid Probes: A Primer for Pathologists*, ASCP Press, Chicago, Illinois, 1989, pp. 49-50.
Fisher, Z., *Physiol. Chem* 60:696-78 (1909).
Ranki et al., *Curr. Top. Microbiol. Immunol.* 104:307-318 (1989).
Ranki et al., *Gene* 21:77-85 (1983).
J. G. J. Bauman et al., "A New Method for Fluorescence Microscopical Localization of Specific DNA Sequences by in situ Hybridization of fluorochrome-Labelled RNA," *Exp. Cell. Res.*, 128:485-499 (1980) (Bauman I).
J. G. J. Bauman et al., Rapid and High Resolution Detection of in situ Hybridization to Polytene Chromosomes Using Fluorochrome-Labelled RNA, *Chromosoma*, (Berl.) 84, pp. 1-18 (1981).
T. R. Broker et al., "Electron Microscopic Visualization fo tRNA Genes With Ferritin-Avidin: Biotin Labels," *Nucl. Acids Res.*, 5, pp. 363-384 (1978).
R. M. K. Dale et al., "The Synthesis and Enzymatic Polymerization of Nucleotides Containing Mercury: Potential Tools for Nculeic Acid Sequencing and Structural Analysis," *Proc. Natl. Acad. Sci. USA*, 70, pp. 2238-2242 (1973) (Dale II).
P. R. Langer, et al., "Enzymatic Synthesis of Biotin-Labelled Polynucleotides": Novel Nucleic Acid Affinity Probes, *Proc. Natl. Acad. Sci., USA*, 78, pp. 6633-6637 (1981).
Drlica, K *Understanding DNA and gene cloning* John Wiley & Sons, Inc. N.Y., 1984, p. 121.

* cited by examiner

ANALYTE DETECTION UTILIZING POLYNUCLEOTIDE SEQUENCES, COMPOSITION, PROCESS AND KIT

CROSS-REFERENCE TO OTHER RELATED APPLICATIONS

This application is a continuation of U.S. patent application Ser. No. 08/342,667, filed on Nov. 21, 1994 (now abandoned), which is a continuation of U.S. patent application Ser. No. 07/805,274, filed on Dec. 10, 1991 (also abandoned), which is a division of U.S. patent application Ser. No. 07/607,787, filed on Oct. 26, 1990 (abandoned). Ser. No. 07/607,787 is a continuation of U.S. patent application Ser. No. 06/922,757, filed on Oct. 24, 1986 (abandoned), which is a continuation of U.S. patent application Ser. No. 06/491,929, filed on May 5, 1983 (abandoned).

BACKGROUND OF THE INVENTION

1. Field of the Invention

The present invention relates to assays, both immunoassays and nucleic acid assays of analytes, which utilize a universal detection system based on polynucleotide interactions.

2. Description of the Prior Art

The analysis and detection of minute quantities of substances in biological and non-biological samples has become a routine practice in clinical and analytical laboratories around the world. Broadly, the analytical techniques can be divided into those based on ligand-receptor interactions (e.g., immunoassay-based techniques), and those based on nucleic acid hybridization (polynucleotide sequence-based techniques).

For example, immunoassay techniques involve, at some stage or step in the process, the non-covalent association between an antibody binding site and an antigen complementary therefor. See, for example, "An Introduction to Radioimmunoassay and Related Techniques" by T. Chard, Elsevier Science Publishers B.V. (Biomedical Division), Amsterdam, N.Y., Oxford, 1978. In polynucleotide sequence-based techniques, the process, at some step or another, involves the non-covalent binding of a polynucleotide sequence to a complementary sequence under hybridization conditions. (See for example, Falkow et al, U.S. Pat. No. 4,358,535, Wahl et al, U.S. Pat. No. 4,302,204, and Heimer, U.S. Pat. No. 3,755,086.)

In a generalized sense, both the aforementioned techniques involve a primary recognition event, brought about by precise molecular alignment and interaction, and energetically favored by the release of non-covalent bonding free energy (e.g., hydrogen bonding, dispersion bonding, ionic bonding, dipolar bonding, and the like). In addition to the primary recognition event, both techniques also involve at one step or another, a signalling event. This step or event relates to the necessity of detecting, in some demonstrable manner to a human or instrument detection system, the primary recognition event.

Signalling has been centered mainly in two broad areas: radioactive and non-radioactive techniques. Radioactive signalling has relied on radiolabeling of one or more components involved in the system, with such atoms as $^{32}P$, $^{131}I$, $^{14}C$, $^{3}H$, and the like. Detection is usually by means of a radioactivity detector. Non-radioactive techniques have been increasingly used in the last few years, since they involve no radioactivity, thus making such techniques safer, cleaner and more stable towards storage. They have been developed to sensitivities as high if not higher than radiolabeling techniques. Among the most common non-radioactive signalling techniques used at present are enzyme linked immunoassays (see, for example, Schuurs, A. H. et al, Clinica Chimica Acta, 81: 1-40 (1977)), fluorescence (Bauman et al, Chromosoma, 84: 1-18 (1981)), indirect immunofluorescence (Rudkin et al, Nature, 265: 472-473 (1977)), avidin-biotin interactions (Manning, J, et al, Biochemistry, 16: 1365-1370 (1977)), electron microscopy of electron dense nuclei such as ferritin (Broker, T. R. et al, Nucleic Acids Research 5: 363-384 (1978)), latex attachment (Sodja, A., ibid 5: 385-401 (1978)), combinations of the aforementioned techniques, and others.

The primary recognition event and the signalling event need to be coupled to each other, directly or indirectly, proportionately or inversely proportionately. Thus, in such systems as nucleic acid hybridizations with radiolabeled probes, the amount of radioactivity is usually directly proportional to the amount of analyte present. The same is true with a system such as a sandwich immunoassay, wherein the amount of labeled second antibody being detected is normally directly proportional to the amount of antigen present in the sample. Inversely proportional techniques include, for example, competitive immunoassays, wherein the amount of detected signal decreases the more analyte present in the sample.

The prior art has also utilized amplification techniques, wherein the signalling event is related to the primary recognition event in a ratio greater than 1:1. Thus, the signalling component of the assay may be present in a ratio of 10:1 to each recognition component, thereby providing a 10-fold increase in sensitivity.

The great versatility polynucleotide sequence-based recognition systems has caused an extensive amount of experimentation and research to be invested therein. This versatility is brought about by the precise alignment of complementary nucleotide bases to each other, adenine (A) aligning to thymidine (T) and guanine aligning with cytidine (C). Given this complementarity, it is possible to utilize any desired sequence to provide an infinitely versatile system.

One of the impediments to a more extensive use of polynucleotide interaction-based systems, however, has been the necessity of attaching signalling or reporter groups (such as radioactive phosphorous, or enzymes, or biotin, or the like) to individual nucleotide residues in the polymer chain. At least two problems arise out of this requirement.

First, the chemical reaction conditions involved in the modification of a polynucleotide polymer are generally too vigorous to be sufficiently selective for any one nucleotide in particular. For example, dicarbonyl reagents such as kethoxal or glyoxal will indiscriminately react with guanine (see for example Shapiro, R. et al, Biochemistry, 5: 2799-2807 (1966), Litt, M, ibid, 8: 3249-3253 (1969), or Politz, S. M. et al, ibid, 20: 372-378 (1981)). Thus, if one were to use a dicarbonyl-based cross-linking agent to attach an enzyme or a low molecular signalling compound directly on a polynucleotide chain, one would risk (and in fact one obtains) modification of a substantial amount of all guanine residues in the chain. This, of course, severely hinders the use of such modified chain in a recognition step. This problem has been solved in the prior art by the use of enzymatic (DNA polymerase-based) incorporation of individual modified nucleotides (previously modified in a non-hydrogen-bond-disruptive manner) into a nascent polynucleotide chain. It would, however, be preferred to utilize chemical modification techniques on the final polynucleotide polymer itself.

A second problem is associated with the attachment of signalling groups to polynucleotides and is somewhat related to the first. The problem is based on the necessity of synthesizing, by sometimes sophisticated and elaborate synthetic techniques, the modified monomeric nucleotide units themselves, prior to their enzymatic incorporation into polymer. Thus, radiolabeled nucleotides or biotin-labelled nucleotides have to be independently synthesized. Further, the amount of incorporation of a chemically modified nucleotide into final nucleic acid polymer may also influence the ability of a probe to recognize a given sequence on the analyte. This is particularly important if amplification techniques are utilized wherein signalling groups greatly outnumber recognition groups.

It would therefore be very useful to develop an assay system which utilizes components that are easily prepared, amenable to chemical modification rather than enzymatic-based reactions, that would utilize the great versatility of polynucleotide-based sequence recognition, and include the possibility of signal amplification methods.

SUMMARY OF THE INVENTION

The present invention provides a universal assay system which takes advantage of polynucleotide sequence recognitions, which allows for the use of chemical modification reactions, which is also capable of utilizing recognition events based on any type of non-bonding interaction, and which can use any of the myriad of available signalling methods.

The process of the invention comprises a method of detecting in a sample an analyte (A) having a molecularly recognizable portion thereon, which comprises:
  providing a molecular bridging entity (B) having thereon
    (i) a portion capable of recognizing said molecularly recognizable portion on said analyte; and
    (ii) a portion comprising a polynucleotide sequence; and
  a signalling entity (C) having thereon
    (i) a polynucleotide portion capable of annealing to said polynucleotide portion of said bridging entity, thereby to form a stable polynucleotide hybrid, and
    (ii) a signal generating portion;
  forming a complex comprising:
    (1) said analyte (A) complexed through said molecularly recognizable portion to
    (2) said recognizing portion of said entity (B); said entity (B) being completed through said polynucleotide portion thereon to
    (3) said polynucleotide portion of said signalling entity; and
  detecting a signal by means of said signal generating portion present in said complex.

The invention provides, in addition to the aforementioned process, various elements and components to be used therein, such as various molecular bridging entities, and various signalling entities, as well as kits comprising said entities, and other components for use in the process.

In essence, the invention is based on the realization that the recognition portion and the signalling portion of the multicomponent assay system should be present on different components of the system, thereby separating them, and avoiding the interference of the signalling portion on the recognition portion. This separation into multi-component entities, also allows the signalling portion to be attached to one of the components by chemical modification techniques, without affecting the recognition component.

Uses for the process, system and components are unlimited, and include all of the uses to which prior art assay techniques have been put, as well as generally, the detection of any analyte capable of recognition, in any sample.

BRIEF DESCRIPTION OF THE FIGURES

The invention will be better understood by reference to the attached Figures wherein:

FIG. 1 represents a generalized scheme for the assay system of the invention. Analyte 1, having a molecularly recognizable portion 2 thereon, is brought into contact with molecular bridging entity 3, having a portion 4 thereon capable of recognizing the molecularly recognizable portion 2 on analyte 1. Bridging entity 3, in addition, carries a portion 5 comprising a polynucleotide sequence, generally denoted as ATCGATC . . . . Also present in the system is signalling entity 6 having thereon a polynucleotide portion 7 capable of annealing to polynucleotide portion 5 of the bridging entity 3. The signalling entity 6 also carries a signal generating portion 8. When analyte is present in the sample being analyzed, interaction occurs with bridging entity 3 through the recognizable and recognition portions 2 and 4, respectively. The complex formed thereby is then annealed through the polynucleotide portion 5 to the complementary polynucleotide portion 7 on the signalling entity, which brings the signalling portion 8 into some stoichiometric relation with the analyte 1.

FIG. 2 shows a preferred system under the broader concept of the invention, wherein analyte 9 comprises a DNA sequence 10 (generally indicated as ATCGATCGATC). Bridging entity 11, shown as a single-stranded circular polynucleotide polymer, carries a recognizing portion 12 which is a DNA sequence complementary to the DNA sequence of the analyte. Bridging entity 11 also carries, in addition, a poly G sequence 13, which is capable of annealing and forming a stable hybrid with complementary poly C sequence 15 on signalling entity 14. Signalling entity 14 also carries a biotin portion 16 as its signal generating group. Presence of the DNA sequence 10 in the sample being analyzed causes the bridging entity 11 to hybridize thereto, and subsequent annealing of the signalling entity to the thus formed complex attaches the biotin portion, through the network, to the analyte. The biotin portion 16 can then be detected, for example by addition of an avidin/enzyme couple, followed by addition of enzyme substrate, and color detection.

DESCRIPTION OF THE PREFERRED EMBODIMENTS

System Components

The term "analyte" as used in the specification and claims includes any substance or substances either alone or in admixtures, which presence is to be detected and, if necessary, quantitated. The analyte may be a molecule of small or high molecular weight, a molecular complex, or a biological system, such as a virus, a cell, or group of cells. Among the common analytes are proteins, polysaccharides, lipopolysaccharides, protein complexes, nucleic acids or segments thereof, either single- or double-stranded, whole viruses or viral components such as cores or capsids, bacteria of various different types, tissue cells, and the like. Among the most common proteins are the structural proteins, enzymes, immunoglobulins, or fragments thereof. Among the most common nucleic acids are DNA and RNA of various different types, such as tRNA, mRNA, rRNA, and the like. Bacteria, either whole or fragments thereof, such as cell walls or other recognizable portions, include both gram positive and gram negative bacteria. Fungi, algae, and other submicroscopic microorganisms are also included, as well as animal (e.g., mammalian) cells.

The analyte should have a "molecularly recognizable portion" thereon. This phrase denotes any molecular portion of the analyte which is capable of being recognized by a complementary molecular portion on the bridging entity of the system. Molecular recognition, as will be understood by those of skill in the art, includes the non-covalent binding in three dimensions between complementary portions of two molecules. A molecularly recognizable portion on an analyte may be, for example, a polynucleotide sequence, such as RNA or DNA, to be recognized by its complementary sequence; an antigen portion, to be recognized by its corresponding monoclonal or polyclonal antibody; an antibody portion, to be recognized by its corresponding antigen; a lectin portion, to be recognized by its sugar; a sugar portion, to be recognized by its lectin; a hormone portion, to be recognized by its receptor; a receptor portion, to be recognized by its hormone; an inhibitor portion, to be recognized by its enzyme; an enzyme portion, to be recognized by its inhibitor; a cofactor portion, to be recognized by a cofactor enzyme binding site; a cofactor enzyme binding site portion, to recognized by its cofactor; binding ligand recognized by its substrate and vice versa (i.e. biotin-avidin); or any permutation or combinations thereof.

Among the most common molecularly recognizable portions are the three-dimensional protein arrangements in antigens of various different sorts, the cell wall structures present in various cells, or the nucleic acid sequences present in the DNA or RNA of organisms.

The second component of the system is the "molecular bridging entity". This entity need only contain a first portion capable of recognizing the molecularly recognizable portion on the analyte, and a second portion which comprises a polynucleotide sequence. These two portions of the bridging entity may be of the same type (i.e., both of them polynucleotide sequences, albeit different ones) or of a different type (one being, for example, an antibody portion and the other the polynucleotide portion.)

The portion on the bridging entity capable of recognizing the molecularly recognizable portion on the analyte must contain a molecule or molecular fragment complementary to the recognizable portion on the analyte. Therefore, if the analyte contains a polynucleotide sequence, the recognizing portion of the bridging entity should be a complementary polynucleotide sequence or "probe". If the molecularly recognizable portion on the analyte is a generalized antigen, the recognizing portion on the bridging entity should be an antibody thereto. The same is true with respect to the complementary pairs sugar/lectin, receptor/hormone, inhibitor/enzyme, and the like, described previously.

The second portion of the molecular bridging entity must comprise a polynucleotide sequence. The polynucleotide sequence can be any chosen sequence, provided that it is long enough to provide stable annealing with a complementary sequence under given stringency conditions, that it be complementary to the polynucleotide sequence on the signalling entity, and, if the recognizing portion on the bridging entity is itself a polynucleotide sequence, that it be sufficiently different from said recognizing sequence portion, to avoid hybrid formation between the analyte sequence and the second polynucleotide portion on the bridging entity. The latter of the three conditions is required to prevent molecular confusion with concomitant appearance of false results.

The second portion polynucleotide sequence on the bridging entity (i.e., the one complementary to the sequence on the signalling entity) may code for a particular gene product or products, or may code for no gene product at all. Thus, any structural gene or portion thereof could be used as the polynucleotide sequence portion on the bridging entity. A preferred sequence, however, would not code for a given gene since such coding may interfere with complementary gene sequences present in the analyte. It is thus preferred to choose polynucleotide sequence portions on the bridging entity which are non-coding, and not likely to be complementary to sequences on the analyte such as, for example, sequences comprising poly deoxy G, poly deoxy A, poly deoxy GT, poly deoxy GA, poly deoxy GAT, poly deoxy GTA, or any other low complexity (repeating) sequence. By "polynucleotide" is meant to include both polyribonucleotides, polydeoxyribonucleotides, or any poly-purine, -pyrimidine or analog and combinations thereof.

Specific, examples of bridging entities as used in this invention are covalently attached entities of monoclonal or polyclonal antibodies with polynucleotides, polynucleotides with polynucleotides, protein antigens with polynucleotides, saccharides with polynucleotides, small molecular weight organic compounds with polynucleotides, lectins with polynucleotides, receptors with polynucleotides, hormones with polynucleotides, enzyme inhibitors with polynucleotides, enzyme cofactors with polynucleotides, and combinations and permutations thereof.

The molecular ratio of the recognizing portion on the bridging entity, to the polynucleotides sequence portion thereon need not necessarily be 1:1. There may be many more polynucleotide sequence portions than recognizing portions, or vice versa. In the case when the ratio of polynucleotide sequence portion to recognizing portion on the bridging entity is greater than 1, for example, 5, 10 or greater, the system amplifies the primary recognition event by a factor equal to the ratio.

Figure 1:
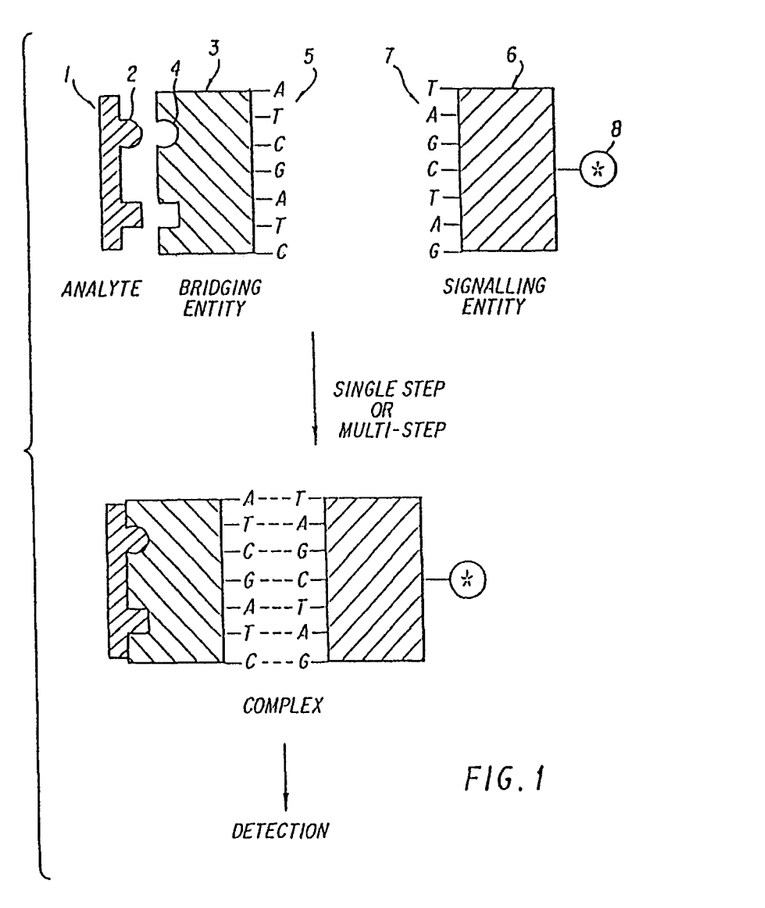
Figure 2:
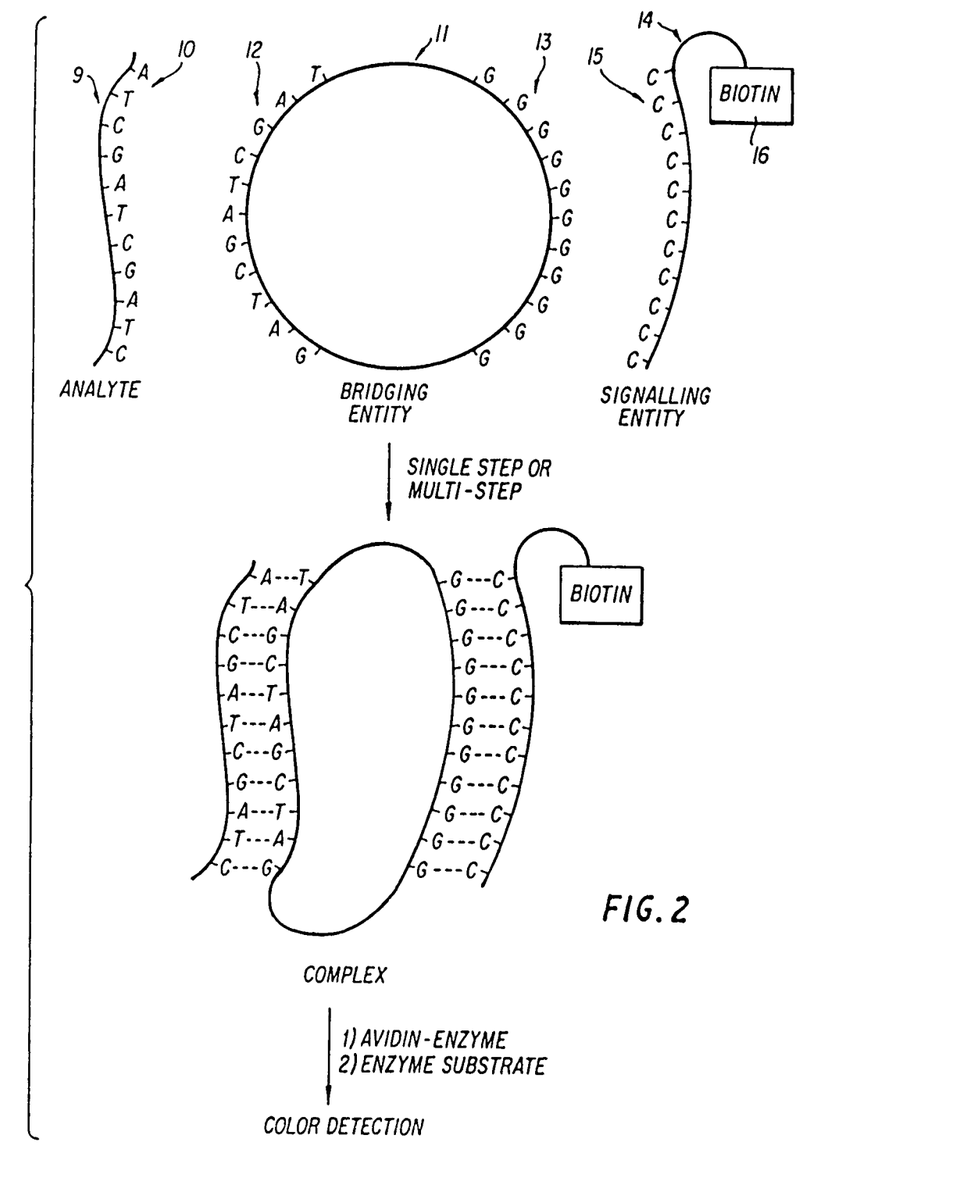

Among preferred bridging entities of the invention are circular polymers of single- or double-stranded DNA. The single-stranded ones include so-called filamentous phages, such as fd, f1 and M13 (see Van Wezenbeek, P., Gene, 11: 129 (1980).) These filamentous phages do not lyse their host; rather, they are released from infected cells as the cells continue to grow and divide. M13 is commercially available (Bethesda Research Labs, Inc.) and has been extensively used as a cloning and sequencing system. It can be cut at a restriction endonuclease site to incorporate therein any desired polynucleotide probe sequence, to serve as the recognizing portion of the bridging entity. Either at the same site or at a different site, the circular DNA can be opened to incorporate the polynucleotide portion of the bridging entity, capable of annealing to the complementary portion on the signalling entity. In this manner, a bridging entity is obtained which is capable or recognizing a gene sequence on an analyte by hybridization, and is also capable of annealing to the signalling entity through another sequence thereon. (A generalized system of this sort is shown in FIG. 2.)

In one particularly preferred embodiment, the bridging entity comprises a DNA polymer which carries the sequence for a given gene (for example, a viral probe such as hepatitis B virus, EBV and the like), and, at another place in the polymer, a poly G, or poly GT, or poly dG, or poly dC, or poly dCA, or poly dGdT polynucleotide portion. Ideally, a single-stranded DNA polymer can be provided carrying the polynucleotide portion capable of annealing to the signalling entity (e.g., poly dGT), and also carrying a restriction endonuclease site, so that the user can incorporate any desired DNA probe thereinto. In this manner, by a few simple enzymatic manipulations, the DNA polymer bridging entity can be quickly transformed into a wide variety of bridging entities.

The signalling entity of the invention needs to carry both a polynucleotide portion capable of annealing to the complementary portion on the bridging entity, and a signal generating portion.

The polynucleotide portion on the signalling entity is defined by the same parameters as the complementary portion on the molecular bridging entity. It should be of a length capable of forming stable polynucleotide hybrids with the corresponding polynucleotide on the bridging entity. "Annealing" as used in this part of the invention refers to the required base pair matching between two complementary polynucleotide strands, under any given set of stringency conditions. It is generally understood in the art that about 12 to 13 nucleotides in a row are necessary for stable annealing. Thus, as a minimum, the number of nucleotides in the sequence should be that necessary for stable annealing with the polynucleotide portion of the bridging entity. The formation of the hybrid should be stable enough to withstand any washing, elution, or signal detection procedures which follow hybridization.

The "signal generating" portion of the signalling entity can encompass virtually any of the signal generating systems used in the prior art, and any system to be developed in the future. It comprises a moiety which generates a signal itself (e.g., a radiolabel), or a moiety which, upon further reaction or manipulation will give rise to a signal (e.g., an enzyme-linked system). Both types are herein called "signal generating" portions.

Thus, the signal generating portion may comprise a radiolabel (e.g., $^{14}C$, $^{32}P$, $^{3}H$, and the like), an enzyme (e.g., peroxidase, alkaline or acid phosphatase, and the like), a bacterial label, a fluorescent label, an antibody (which may be used in a double antibody system), an antigen (to be used with a labeled antibody), a small molecule such as biotin (to be used with an avidin, streptavidin, or antibiotin system), a latex particle (to be used in a buoyancy or latex agglutination system), an electron dense compound such as ferritin (to be used with electron microscopy), or any combinations or permutations thereof.

For example, if the signal generating portion of the signalling entity is an antigen, a signal can be generated by complexing said antigen with an antibody/enzyme conjugate, followed by addition of enzyme substrate. If the signal generating portion of the signalling entity were an antibody, signal can be generated by complexing anti-antibody or an $F_C$ binding protein such as Protein A therewith, which second antibody or Protein A have been conjugated to an enzyme.

Among the preferred signal generating portions are those based on the biotin/avidin system. This system can be incorporated into the signalling entity by a variety of means. For example, the polynucleotide portion of the signalling entity can be covalently attached to biotin via a cytochrome c bridge (Manning et al, Biochemistry, 16: 1364-1370 (1977), Manning et al, Chromosoma, 53: 107-117 (1975), Sodja, A., Nucleic Acids Research, 5: 385-401 (1978)), or the biotin can be covalently incorporated into specific nucleotide residues (Langer, P. R., Proceedings of the National Academy of Sciences, USA, 78: 6633-6637 (1981)), or the biotin can be attached to a polynucleotide by means of a diamine (e.g., pentane diamine) bridge (Broker, T. R., et al, Nucleic Acids Research 5: 363-384. (1978)). Interaction of the biotin molecules in the signal generating portion with avidin, streptavidin or anti-biotin antibodies is then carried out, wherein the avidin, streptavidin or the antibodies are conjugated to such signalling components as latex particles (Sodja, A., et al, supra, or Manning, et al Chromosoma, supra), ferritin (Broker, supra), a fluorogen such as fluorescein, an enzyme, or the like.

A thorough description of various non-radioactive signal generating systems, both biotin/avidin-based and nonbiotin/avidin-based can be found in U.S. Pat. Nos. 5,328,824; 5,449,767; 5,476,928; 4,711,955 and 5,241,060. The first patent, Ward et al., U.S. Pat. No. 5,328,824, titled "Methods of Using Labeled Nucleotides," issued on Jul. 12, 1994, based on Ser. No. 07/130,070, filed on Dec. 8, 1987, which is a division of Ser. No. 06/496,915, filed on May 23, 1983, the latter application having also issued on Dec. 8, 1987 as the fourth listed patent, Ward et al., U.S. Pat. No. 4,711,955, being titled "Modified Nucleotides and Methods of Preparing and Using Same." Ser. No. 06/496,915 is a continuation of Ser. No. 06/255,223, filed Apr. 17, 1981, abandoned. The second patent, Ward et al., U.S. Pat. No. 5,449,767, titled "Modified Polynucleotides and Methods of Preparing Same," issued on Sep. 12, 1995, based on Ser. No. 07/886,660, filed on May 20, 1992, which is a continuation of Ser. No. 07/130,002, filed on Dec. 8, 1987, the latter being a division of the aforementioned Ser. No. 06/496,915. The third patent, Ward et al., U.S. Pat. No. 5,476,928, titled "Modified Nucleotides And Polynucleotides And Complexes Formed Therefrom," issued on Dec. 19, 1995, based on Ser. No. 07/841,910, filed on Feb. 26, 1992, which is a continuation of the aforementioned Ser. No. 07/130,002. The fifth patent, Engelhardt et al., U.S. Pat. No. 5,241,060, titled "Base Moiety-Labeled Nucleotide," issued on Aug. 31, 1994, based on Ser. No. 07/532,704, filed on Jun. 4, 1990, which is a division of Ser. No. 07/140,980, filed Jan. 5, 1988, abandoned, which is a continuation of Ser. No. 06/674,352, filed Nov. 21, 1984, abandoned, which is a continuation application of Ser. No. 06/391,440, filed Jun. 23, 1982, also abandoned. The contents of the aforementioned U.S. Pat. Nos. 5,328,824; 5,449,767; 5,476,928; 4,711,955 and 5,241,060, are herein fully incorporated by reference.

In addition, the polynucleotide portion of the signalling entity need not be a polynucleotide which has been chemically modified or artificially altered in any way. Some biological systems perform in vivo modifications which can be utilized by this system. One such system is the phage $T_4$ grown in *E. coli*. $T_4$ DNA has a very high content of glycosylated C residues. It is possible to insert (clone) a low complexity repeating polynucleotide sequence into phage $T_4$. This phage would then be naturally propagated and glycosylated in the host. The viral DNA can be isolated from *E. coli* and bound to a complementary sequence on the bridging moiety. Detection could then be accomplished via a lectin/enzyme system, or lectin/fluorescent dye, or lectin/electron dense material, or lectin/radioactive label, using the natural glucose residues on the $T_4$ DNA as points of anchorage. Other T (even) phages such as $T_2$, $T_6$, or $T_8$ can also be used.

The number of signal generating portions need not have a 1:1 stoichiometry with the number of polynucleotide portions on the signalling entity. When the ratio of signal generating portions to polynucleotide portion in the signalling portion of the signalling entity is greater than 1 (e.g. greater than 5, or greater than 10), the system functions as an amplification system. Thus, for example, if there are 10 signal generating portions per polynucleotide portion in the signalling entity, a 10:1 signal amplification over the bridging entity is obtained. If, in addition, the bridging entity has a signal amplification system itself, i.e., the ratio of polynucleotide portions to recognizing portions on the bridging entity is greater than 1, the overall signal amplification system is the product of both ratios. This means that for every primary recognition event occurring at the level of analyte, the amplification quickly increases and leads to very sensitive systems. This factor can be readily controlled by the design of the system components.

Processes of Preparation

The bridging entity, as stated previously, needs to comprise a recognizing portion and a polynucleotide portion. The signalling entity requires a polynucleotide portion and a signal generating portion. Thus, generally, the method of preparation of individual components in the system will relate to the covalent attachment of polynucleotides, or individual components thereof, to 1) protein moieties, 2) saccharide moieties, 3) other polynucleotide moieties, 4) small molecular weight compounds (e.g., MW less than about 1000), 5) radiolabels, or 6) insoluble phases such as bacterial particles, or latex particles. Therefore, the chemistry involved in the covalent attachment or conjugation of nucleic acids to their corresponding partner or partners is well within the skill of the art.

The covalent attachment of polynucleotide sequences to proteins is well described in the literature. Normally, the reaction is carried out directly by carbodiimide crosslinking (Halloran, M. K. J. Immunol. 373 (1966) or by cross-linking the protein to the nucleic acid in the presence of such agents as formaldehyde (see e.g., Brutlag, D. et al, Biochemistry, 8: 3214-3218 (1969), Manning, J. E., et al, Chromosoma, 53: 107-117 (1975)), (4-azidophenyl) glyoxal (Politz, S. M., Biochemistry, 20: 372-378 (1981)); by oxidation of 2',3'-hydroxy ends of a polyribonucleotide, followed by i) Schiff base formation with the amine groups of a protein, and by ii) borohydride reduction (Sodja, A., et al, Nucleic Acids Research, 5: 385-401 (1978)). Other methods include direct bromination of DNA (Jones, A. S., Nature 183: 1603 (1959) followed by reaction with diaminohexane (Lowe, C. R., Eur. J. Biochem. 73: 265-274, (1977)), and coupling via protein carboxyl functions; or by mercuration of cytosine moieties (Dale, R. M. K. et al, P.N.A.S., 70: 2236-2242, (1973)) followed by halogenation (Dale, R. M. K. et al, Nucleic Acids Res. 2:915-930 (1975)), reaction with diaminohexane and coupling to protein carboxyl groups.

Of particular interest is the use of dicarbonyl reagents for chemical modification of guanine bases in the preparation of the signalling entity. This represents one of the particularly useful advantages of the present multi-component assay system. If the polynucleotide portion on the signalling entity has very low G content, it is possible to chemically react said polynucleotide portion with any material via a cross-linking agent such as a dicarbonyl compound, without fear of irreversibly modifying the annealing properties of the polynucleotide portion in question. This applies equally well to the attachment of any small molecular weight molecule to the polynucleotide portion, which attachment depends on the use of dicarbonyl compounds, or other nondiscriminating cross-linking agents. This technique saves the effort and time involved in previously modifying individual nucleotide residues, and then incorporating these into a polynucleotide strand by enzymatic polymerization.

The attachment of polynucleotide sequences to saccharides can be carried out according to Cramer et al, Chem. Ber 92: 384-391 (1959). Saccharides having up to 20 saccharide units are preferred.

The attachment of polynucleotide sequences to other polynucleotide sequences is carried out by either chemical or enzymatic techniques, such as using blunt end ligation or ligation based on the presence of cohesive terminii generated by endonuclease digestion enzymes. The cleavage and ligation of DNA sequences to each other is well described in Helling and Lomax, "The Molecular Cloning of Genes—General Procedures" which is Chapter 1 of "Genetic Engineering" by Chakrabarty, CRC Press, 1978, pages 1-30.

Other methods for attaching polynucleotides to polynucleotides include using SS Dna+Ribo dUTP+Terminal Transferase (Roychoudery, R.+Wu, R., in Meth. in Enz., LXV, 43, (1980)); Periodate oxidation, reductive amination with amino derivatives including 1,6 diamino hexane (1); 3-aminopropionic acid (2), or bis(2-amino ethanethiol) (3), (Perikeh, I Mach, S, and Cuatrecasas, in Meth. in Enz. XXXIV, 82 (1974)); or by limited bromination of C (through mercuration) (Dale & Ward supra) and subsequent reaction of DNA with same reagents ((1), (2)+(3)).

DNA derivatives of compounds (1) or (2), above, can subsequently be coupled to proteins via water-soluble carbodiimide derivatives (Inman, J. K. in Meth in Enz., XXXIV, 52-53) (1974). In case (3), the protein can be activated with the N-hydroxy succinimide ester of bromoacetic acid. The resulting activated protein can be covalently linked to the thiolated nucleic acid at room temperature.

The covalent incorporation of radiolabels such as $^{32}$P into DNA sequences can be done by any of a variety of methods, such as direct incorporation of radiolabeled nucleotides by enzymatic polymerization, nick translation, and the like (Rigby et al, J. Mol. Biol. 113: 237-251 (1977).)

The preparation of the individual elements of the signal generating system such as protein/latex conjugates, protein/ferritin conjugates, antibody/enzyme conjugates, fluorogen/antibody conjugates, avidin/enzyme conjugates, and the like is generally well known in the art and will be not described in further detail.

The specific preparation of individual polynucleotide sequences is also well understood by those of skill in the art. For example, if a polynucleotide sequence comprises a gene or genes, the same can be prepared by synthetic procedures, or can be prepared by reverse transcription of mRNA using reverse transcriptase to generate a complementary DNA. If the polynucleotide sequence comprises a strand of any one nucleotide (e.g., poly dG or poly dC) or a strand of any dinucleotide pair (e.g., poly dGT, or the like), the same can be readily prepared by enzymatic-based reactions such as by using DNA polymerase, or by synthetic methodology.

Methods of Use

The analyte being detected can be present in any biological or non-biological sample, such as clinical samples, for example, blood, urine, feces, saliva, pus, semen, serum, other tissues, fermentation broths, culture media, and the like.

If necessary, the analyte is preextracted or purified by methods known to concentrate the particular type of analyte from its admixing components. For example, if the analyte is a protein or protein-containing fraction, protein extraction procedures such as salt precipitations, alcohol precipitations or chromatography can be utilized. If the analyte comprises a nucleic acid segment to be identified, nucleic acid extraction procedures, such as phenol extraction, can be utilized. The analyte, together with impurifying materials if such be the case, can be tested in the mixture as purified or, especially when it is a nucleic acid segment, can be immobilized (see for example, Wahl et al U.S. Pat. No. 4,302,204.)

The composition suspected of containing the analyte is incubated with the bridging entity for a time and under conditions sufficient to allow complexation between the recognizable portion of the analyte and the recognizing portion on the bridging entity. These conditions will vary depending on the nature and amount of the analyte and of the bridging entity. Normally, after complexation has occurred, the sample is washed with neutral solution to remove excess bridging entity. Alternatively, no wash is carried out at this stage but signalling entity is added to the mixture and a wash is carried out after annealing has occurred between the polynucleotide strands on the bridging entity and on the signalling entity respectively. Hybridization of the bridging entity strand to the signalling entity strand is carried out under hybridizing conditions and under any set of stringency conditions. A final wash may be necessary prior to generation of signal.

Signal generation is carried out by any given technique, depending on the nature of the signal generating system. Thus, if an enzyme linked assay is utilized, the ternary complex between analyte, bridging entity and signalling entity is allowed to incubate with the enzyme carrying reagent (e.g., enzyme/antibody conjugate), and substrate is added thereto to develop color. Alternatively, enzyme might be attached directly to the polynucleotide strand on the signalling entity, in which case substrate is added immediately thereafter to obtain color development. If the signal generating portion of the signalling entity is a biotin moiety, then a biotin reactive molecule such as avidin, streptavidin or anti-biotin antibody, is added thereto. The biotin reactive molecule is conjugated to an enzyme, a fluorescent compound, an electron dense compound, or an insoluble solid phase, and detection is carried out by appropriate means.

Applications

The applications of the system of the invention are unlimited. Any analyte desired to be detected and analyzed in any sample can be subject to the method of the invention.

For example, the system can be used for microorganism detection and identification, by using any of a variety of recognizable portions and recognizing portions in the analyte and the bridging entity respectively.

Of particular interest is the detection and identification of viral and bacterial DNA sequences.

The method can be utilized to diagnose genetic disorders by preparing a polynucleotide complementary to a DNA gene sequence which is associated with the genetic disorder, and detecting the presence of any primary recognition events. Among these genetic diseases, for example, can be mentioned thalassemia. The determination of thalassemia can be made (for known genetic defects) by hybridization of oligonucleotides to genomic DNA followed by specific washing procedures or by restriction analysis and Southern, Northern, or Dot blots.

Another use for the system of the invention is in chromosomal karyotyping, which comprises using a series of modified polynucleotides corresponding to a series of defined genetic sequences located on chromosomes, and then detecting primary recognition events thereon.

Another use includes a method for identifying or locating hormone receptor sites on the surface of cells, which comprises binding a hormone receptor binding compound present in the bridging entity to the receptor site, and then detecting primary recognition events by means of the signalling system of the invention.

Another use comprises the detection of cancer, by detecting in the blood or serum of suspect subjects, the presence of cancer associated antigens such as CEA (carcinoembryonic antigen). Another use includes a method of tumor or cancer cell identification or detection which comprises identifying malignant cells by detecting the absence of normal receptors sites by the technique of the invention.

Another use includes a method of detecting antibodies against certain infectious diseases in animals, by using antigen therefor as a recognizing portion in the molecular bridging entity. Sugar levels or differential glycosylated hemoglobin levels can be detected in diabetes by using a lectin as the recognizing portion on the molecular bridging entity.

Yet another use for the process and system of the invention is in the insolubilization of analytes. Thus, if a sample is suspected of containing an analyte, and one wishes to extract and purify the analyte from the sample, the "signalling entity" is designed so that the signal generating portion comprises or is capable of specifically binding to an insoluble solid phase, such as a natural or synthetic aqueous insoluble resin, a glass, a plastic such as an acrylate or methacrylate, the inside of a test tube wall, or of a well, and the like. The bridging entity is allowed to incubate with the solid phase, thus creating recognition sites (i.e., affinity surfaces) for the analyte, which is then bound thereto.

The present invention lends itself readily to the preparation of kits comprising one or more of the elements necessary to perform the detection and identification process. Thus, a kit may comprise a carrier being compartmentalized to receive in close confinement therein one or more container means or series of container means such as test tubes, vials, flasks, bottles, syringes, or the like. A first of said container means or series of container means may contain the bridging entity, for recognition of any of a wide variety of analytes. A second container means or series of container means may contain signaling entities. A third container means or series of container means may contain predetermined amounts of analyte, so as to provide the ability to construct a standard curve into which results can be interpolated. Other container means or series of container means may contain the elements necessary to generate the signal, such as enzyme linked conjugates, avidin linked conjugates, ferritin linked conjugates, latex linked conjugates, fluorogen linked conjugates, and the like.

In a preferred embodiment, the kit carrier contains a first container means comprising a bridging system which is DNA carrying a polynucleotide portion of predetermined sequence and a restriction site or cleavage site on the DNA which can be used to incorporate any of a number of gene probes for testing and identifying genetic sequences associated with the analyte. Another container means in this preferred kit would comprise a signalling entity carrying a polynucleotide portion complementary to the polynucleotide portion present in the DNA present in the first container means, and a signal generating portion which may be any of the aforementioned systems. A third container means or series of container means in this preferred kit may comprise a variety of DNA probes complementary to the genetic sequences present on one or more polynucleotide-containing analytes such as viruses, bacteria, cells and the like.

Thus, the user would utilize a cleavage method (such as use of a restriction endonuclease) to open the DNA in the first container, incorporate thereinto any desired DNA probe present in the third container or container series, ligate the polymer and then utilize the bridging entity and the signalling entity to detect and identify the presence of any desired genetic sequence present in the analyte. It should be kept in mind that a single strand cannot be cut with a restriction enzyme unless a linker (which spans the site) is first hybridized to it, thereby creating a double-strand in that location. Normally the gene would be ligated into the RF (double-stranded) so that it could be amplified in a microorganism.

Having now generally described this invention, the same will be illustrated by reference to certain specific embodiments which are included herein for purposes of illustration only and are not intended to be limiting unless otherwise specified.

EXAMPLES

Examples 1-31 relate to processes of preparation of bridging and signalling moieties. The examples show preparation methods which may be classified within the following categories:

1) Chemical activation of oligonucleotides for subsequent coupling to proteins, saccharides and small molecules.
2) Chemical activation of proteins for subsequent coupling to DNA, saccharides and small molecules.
3) Chemical activation of saccharides for subsequent coupling to DNA, protein and small molecules.
4) Chemical activation of small molecules for subsequent coupling to DNA and protein.
5) Coupling of DNA to protein, saccharides and small molecules.

The examples classified within the above categories are as follows:

1) Chemical Activation of Oligonucleotides.
  A. By terminal ribonucleotide labelling followed by periodic oxidation and reductive amination: Examples 11, 12;
  B. By non-specific bromination: Examples 28, 29, 30.
  C. By specific activation of cytosine moieties via 5-iodocytosine: Examples 16, 17, 18.
  D. By specific activation of guanosine moieties via reaction with 3,4,5-trichlorodiazobenzene: Example 1.
  E. By specific activation of adenosine and guanosine-moieties via reaction with 2,3-dibromopropanal: Example 9.
2) Chemical Activation of Proteins
  A. By bromoacetylation: Examples 13, 14.
3) Activation of Saccharides
  A. By activation of reducing saccharides: Examples 4, 5, 6.
  B. By activation of non-reducing saccharides: Examples 7, 8.
4) Activation of Small Moieties
  A. Biotin: Examples 2, 33, 23, 24, 25, 26
  B. DCTA: Example 3.
5) Coupling of DNA to Protein, Saccharides and Small Molecules
  A. To protein: Examples 15, 19, 20.
  B. Saccharides: Example 19, 18.
  C. To small molecules: Examples 19, 10, 21, 27.

Example 1

Activation of DNA with 3,4,5-Trichloroaniline 100 mg of 3,4,5-trichloroaniline were dissolved in 2.5 ml of 0.5M HCl in 50% DMSO and cooled on ice, under vigorous stirring, an equimolar amount of $NaNO_2$ from a cold 1M solution were added, as rapidly as possible, and then stirring was continued for 10 minutes. 1 mg of 3H or fd DNA in 300 μl of water were mixed with 300 μl of 2M cacodylate buffer pH 6.6 and 500 μl DMSO. (By addition of DMSO the pH of the solution rises to 8.3). 20 μl of the freshly prepared diazonium solution were added thereto and the mixture was incubated for two hours at room temperature. The slight precipitate which appeared during the incubation was removed by centrifugation. The solution was then made 0.4 M with ammonium acetate and the DNA was precipitated with ethanol.

Example 1a

Reaction of Trichloroaniline-Activated DNA with Thiols

Example of Reaction with DCTA-SH and Thiol Activated Mannose

Fd DNA activated with 3,4,5-Trichloroaniline (Example 1) was dissolved in 0.1M sodium hydroxide with an equal amount of 0.1M $K_2HPO_4$. This solution was treated with an equal volume of 0.1M DCTA-SH (Example 3) or thiol activated mannose (Ex. 6 and 9), and incubated under argon at 65° for 2 hours. The precipitated disulfides were removed by centrifugation and the DNA was purified by G50 chromatography and stored at −20° C. Using radioactive Ni to level the derivatized DNA, it was determined that 60% of guanines had been labelled.

Example 2

Biotin-SH

Three millimoles of Biotin-NHS ester were dissolved in 25 ml of anhydrous DMF and mixed with a 1M solution of cysteamine hydrochloride in 12 ml of 0.5M sodium bicarbonate and the mixture was incubated at room temperature overnight. During the incubation a heavy precipitate appeared. The liquid was removed under reduced pressure at 45° C. and the residue was suspended in 50 ml absolute ethanol, 1 g of $NaBH_4$ was added and the suspension was stirred for one hour at 75° C. The ethanol was removed and cold 1 M HCl was added to bring the pH to 4.5, and the water was removed under reduced pressure at 35° C. (All these operations were performed under an argon atmosphere to prevent oxidation of the thiol.) The solid residue was powdered and triturated with 4 ml of cold deareated 0.01 M acetic acid. These procedure was repeated twice and the residue was lyophilized. TLC chromatography showed that the main biotin spot contained thiol; two minor spots were thiol negative. In all reactions the amount of biotin used was based on the thiol content.

Example 3

DCTA-SH

One milimole of DCTA-bromide was added to 5 ml of 50% DMF containing 0.2 ml of 2,3-dithioethylene and 0.5 ml of triethylamine. The mixture was incubated under argon for 2 hours at 60-70° C. The solution was then mixed with 20 ml of water and loaded onto a Dowex AG-1 column of 9 ml bed volume. The column was washed with 50 ml of 0.1M acetic acid solution until the flowthrough was thiol free. The DCTA-SH was then eluted with 0.25M HCl. The thiol containing fractions were combined, evaporated to dryness under reduced pressure at 40° C. and the free acid (300 mg) was stored at −20° C. under argon.

Example 4

1-0-Methyl-6-0-Tosyl-α-D-mannopyranoside

Non-reducing saccharides were activated through the primary alcohol group by forming the tosylate, and displacing it with ammonia to form an amino group, or with a dithiol to form a thiol group. An example is described here, the activation of α-methyl-d-mannoside, a non-reducing sugar and of mannose as a reducing one. The tosylation was performed analogous to a published procedure (F. Cramer et al. Chem. Ber. 92, 384-391 (1979).)

23 g of methyl-D-mannoside were dissolved in 400 ml of absolute pyridine and the solution was cooled to −15° C. on an ice salt mixture. A solution of 24.6 g of p-Toluene sulfonyl chloride in 80 ml absolute pyridine was added to the vigorously stirred mixture and reacted at −15° C. for 30 minutes and 12 hours at 20° C. The pyridine was removed under reduced pressure at 40° C. and the residue was dissolved in chloroform. The solution was warmed to 50° C. and washed successively with 0.5 M potassium hydrogen sulfate followed by 0.5M potassium bicarbonate solution at 50° C. (the 50 degree temperature was necessary to avoid gel formation).

Example 5

6-amino-α-methyl-D-mannoside hydrochloride

A solution of 6 g of the tosylate (Example 4) in 130 ml absolute methanol was saturated at 1° C. with dry ammonia and autoclaved for 16 hours at 120° C. The dark reaction product was refluxed with charcoal and methanol was removed by distillation leaving a slight yellow syrup. The syrup was dissolved in water and the sulfonate liberated during the displacement reaction was removed by passing the solution through an anions exchanger. HCl was added to the eluate to bring the pH to 5.0 and the water was removed under reduced pressure at 40° C. The residue was triturated with a mixture of 15 ml of absolute methanol and 15 ml of absolute ether and the solid material was dissolved in 50 ml of absolute methanol and cooled, the addition of 25 ml absolute ether initiated crystallization, yielding 2.5 g hydrochloride.

Example 6

S-(2-mercaptoethyl)-6-thio-α-D-methyl-mannopyranoside 6 g of the sugar tosylate (Example 4) were dissolved in 250 ml of absolute methanol containing 20 ml of a freshly prepared solution of sodium methoxide. To the mixture was added 5 ml of 1.2 ethanedithiol. The mixture was autoclaved at 120° C. for 10 hour and the reactions product was treated as above. Yield 3.1 g.

Example 7

2,3,4,6, Tetraacetyl-α-D-mannopyranosyl chloride

This compound was prepared analogously to a published procedure (D. Horton, Organic Synthesis Vol 46 p. 1, Wiley N.Y. 1966). 25 g of dried mannose were added slowly with stirring to 60 ml of acetyl chloride. The vessel was connected to a reflux condenser and the mixture was stirred for 16 hours at room temperature. Chloroform, 300 ml, was added through the condenser and the mixture was poured with vigorous stirring onto 300 g of ice and 100 ml of water. The mixture was transferred to a separatory funnel, and the organic phase was poured as fast as possible into a beaker containing ice and 300 ml of saturated sodium bicarbonate solution. The organic phase was separated and dried with 25 g of anhydrous magnesium sulfate. The drying agent was removed, washed with dry alcohol free chloroform and the combined chloroform solution was concentrated to 35 ml at a reduced pressure in a rotatory evaporator. At 50° C. ether was added to the solution until slightly turbid and the solution left at room temperature. The crystals were removed by filtration and washed with dry ether. Yield 39 g.

Example 8

S-(2-mercaptoethyl)-1-β-D-mannopyranosyl sulfide and S-(2-aminoethyl)-1-β-D-mannopyranosylsulfide To a solution of 10 g acetochloromannose (Example 7) in 60 ml anhydrous DMF, 4 ml of 1.2 ethanedithiol or 5 g cysteamine hydrochloride and 5 of fine powdered sodium carbonate were added to the suspension which was stirred under argon for 6 hours at 70° C. The carbonate was removed and the liquid was evaporated under reduced pressure at 45° C. The residue was dissolved in absolute methanol and freshly prepared 0.1 M sodium methoxide was added to bring the pH to 8.0 and the mixture was stirred for 5 hours at room temperature. 2 ml of glacial acetic acid were added and the liquid was removed under reduced pressure. The residue was recrystallized from acetic acid. Yield 3.1 g.

Example 9

Activation of DNA with 1,2 dibromopropanal

A solution of acrolein (1.7 g) in ether was cooled on an ice bath and 1.3 ml of bromine were slowly added under stirring while waiting for the color to disappear for the next bromine addition. The ether was partially removed by blowing argon over the solution, resulting in a 2 M solution of the 1,2-dibromopropanal (Example 8). The DNA used for the following operations was in the triethylammonium form to facilitate solution in DMF.

0.5 mg of 3H fd-DNA (linear) (partly tritiated) in 250 µl of water were mixed with 3.0 ml of 0.5 M triethylammonium acetate, pH 4.5 in 70% ethanol and 50 µl of the dibromopropanal solution was added. The mixture was stirred in the dark at 37° C. for 40 hours. The reaction was monitored by the appearance of fluorescence. The reaction mixture was evaporated to dryness under reduced pressure, and the DNA dissolved in 0.6 ml water and desalted by G 50 filtration with water as the eluant. The fractions containing radioactivity were combined and the volume was reduced to 0.2 ml.

Example 10

Labelling of the 3,4,5-trichloroaniline DNA with DCTA-SH 0.5 mg of the activated DNA (Example 1) in 0.2 ml of water were mixed with 2.0 ml of 0.5 M triethylammonium acetate in 90% DMF and 50 mg of DCTA-SH in the triethylammonium form were added. The mixture was stirred in the dark for 4 hours at 50° C. The DMF was removed under reduced pressure at 45° C. and the DNA was desalted by G-50 filtration. The degree of labeling was then determined by the use of radioactive $^{63}$Ni. On the average every 5.3 bases were labelled, by calculation.

Similar procedures were used for the biotination and glycosylation of the activated DNA using the thio derivatives of these substances (Examples 2, 6 and 8).

Chemical Labelling of DNA

Rationale

Guanosine couples with certain diazonium salts at the 8 position to give stable colored products (H. Fischer, Z.

Physiol. Chem. 60, 69-78, (1909)), and at position 2 to form yellow products which are acid labile (H. Kossel, Z. Physiol. Chem. 340, 210, 1965, E. N. Moudrianakis et al, Biochim. Biophys. Acta 95, 421 (1966)). The guanosine residues in the single stranded nucleic acids can couple with diazonium salts and this reaction has been used to fix single stranded nucleic acids to cellulose (J. C. Alwine et al. Methods in Enzymology Vol. 68. p. 220-242, 1979)). If the coupled diazonium compound contains an active group that can be easily substituted by thiols or amines, then this constitutes an easy method to attach biotin or other groups to single stranded nucleic acids. 3,4,5-trichlorophenyl diazonium chloride is such a substance which has been used by the inventors to add biotin, 1,2-diaminocyclohexane-N,N,N,N-tetraacetic acid (DCTA), and some sugars to a single stranded DNA.

Another possibility to label single stranded nucleic acids is based on the fact that chloroacetaldehyde reacts with adenine at pH 4.5 to form a fluorescent etheno derivative (under mild conditions). J. R. Barrio, et al Biochem. Biophys. Res. Commun. 46, 597-604, 1972), cytidine reacts at pH 3.5 and guanine at pH 6.5. At pH 4.5 guanidine does not react at all (P. D. Sattsangi, et al, J. Org. Chem., 42, 3292-3296, (1977).)

By using 1,2 dibromopropanal in place of chloroacetaldehyde it was possible to derivatize DNA with an active primary bromide group, which, under mild reaction conditions, reacts with thiol or amine derivatives, offering another method of labeling DNA. These two methods are base specific.

Example 11

Terminal Addition of 5'-uridine Monophosphate (UMP) to Linear 3H fd-DNA with Terminal Transferase and 5'-uridine Triphosphate The incubation mixture of 600 µl contained: 400 µg of DNA, 1 mM $CoCl_2$, 0.2 mM dithiolthreitol, 0.1 M cacodylic acid, 25 mM tris base, 1 mM UTP and 400 units of terminal transferase. The final pH of the mixture was 6.9-7.0.

The mixture was incubated for 2 hours at 35° C. The DNA was precipitated with ethanol and dissolved in 400 µl 0.2 M sodium acetate pH 4.7.

Example 12

Oxidation of the Terminal Ribo Group and Reductive Amination

Synthesis of Amino, Carboxy and Thio-End Substituted DNA

The incubation mixture of 450 µl contained: 400 µg terminal labeled DNA (Example 11), 0.2 M sodium acetate pH 4.7 and 0.1 M $NaIO_4$. It was incubated for two hours at room temperature in the dark and the mixture was passed through a G 50 column equilibrated in 0.3 M potassium borate pH 9.0-9.3, fractions of 0.2 ml were collected. All radioactive fractions were combined in a total volume 1.2 ml. The DNA solution was made 0.4 M with one of the amino components (ε-aminocaproic acid, cysteamine, or 1,6-diaminohexane, using a stock solution of 1 M which was adjusted to pH 9.3), and was incubated in the dark for 90 minutes at room temperature.

The resulting Schiff base was reduced with $NaBH_4$ as follows: $NaBH_4$ freshly dissolved to 0.2 M in water (1 ml) to M was added in four portions over 30 minute intervals. The incubation was continued for a total of 3 hours. The salts and the excess of the amino component were removed by G 50 filtration in a column equilibrated in 0.4 M sodium acetate containing 1 mM beta-mercaptoethanol, the DNA-containing fractions were then combined and stored over argon at −70° C. Before use, DNA was precipitated with ethanol and dissolved in the desired buffer.

Example 13

Activation of Bromoacetic Acid N-hydroxysuccinimide Ester

The NHS (N-hydroxy succinimide) ester of bromoacetic acid was prepared as follows: 100 mmoles of (13.9 g) of bromoacetic acid were dissolved in 50 ml of anhydrous DMF, to this solution 100 mmoles (20.6 g) of N—N-Dicyclohexylcarbodiimide were added with stirring followed by 100 mmoles of N-hydroxysuccinimide (11.9 g adjusted for 100% purity), and the mixture was stirred for 6 hours at 37° C. The mixture was then placed for 2 hours at −20° C. to accelerate the precipitation of hydroxyurea, which was removed by filtration. In the filtrate the DMF was removed under reduced pressure at 45° C. and the active ester was recrystallized from 2-propanal.

Example 14

Bromoacetylation of IgG

IgG (20 mg/ml) in 0.3M potassium borate buffer pH 9.9 was mixed with 0.06 vol of a 10 mg/ml solution of the NHS ester of bromoacetic acid (Example 13) in DMSO, and the mixture was gently mixed for 1 hour at room temperature. The sample was then dialyzed against 0.1 M NaCl 0.1M phosphate buffer pH 7.5.

Example 15

Synthesis of DNA-IgG Conjugates 1.6 mg/ml of bromoacetylated IgG (Example 14) in 0.3 M potassium borate buffer were incubated at room temperature under argon with a thio-substituted, end labeled DNA solution (Example 12) of 3 mg/ml for 2 hours. Mercaptoethanol 0.01 M was then added and the mixture was further incubated at the same temperature for 2 hours to quench the unreacted bromine residues. The solution was then adsorbed on a Protein A column, and the unconjugated DNA was eluted with 1.0 M NaCl. The DNA-IgG conjugate and the unreacted IgG were eluted with isothiocyanate, and dialyzed against 0.1M phosphate buffer, pH 7.2 to remove isothiocyanate. The conjugated IgG and the free IgG were then precipitated with ammonium sulfate 50%, the pellet dissolved in 1.0 ml phosphate buffer and the free IgG was separated from the conjugated IgG by fractionation on a Bio-Gel p-300 column equilibrated in 0.01M NaCl, 0.1M phosphate pH 7.2.

Example 16

Mercuration of pBR322 pBR322 DNA (100 µg) dissolved in 1 ml of 5 mM sodium acetate pH 7.5 containing mercuric acetate (3 mg, 0.01 mmol) was reacted for 4 hours at 50° C. according to a procedure of Dale et al (Nucl. Acid Res. 2:915, 1975). The 5-cytosine mercurated DNA was exhaustively dialyzed in 0.01 M Tris HCl, pH 7.5, containing 0.02 sodium chloride 2 mM EDTA.

Example 17

Iodination of Mercurated pBR 322 DNA

To the mercurated DNA from the previous experiment in 1 ml 0.1M Tris HCl pH 7.5 was added 1 mg iodine using the procedure of Dale et al (Nucl. Acid Res. 2, 915, 1975). After reaction at 20° C. for 2 hours the excess $I_2$ was extracted with chloroform and the iodinated DNA was dialyzed against 0.01 m Tris HCl pH 7.5 containing 0.02M sodium chloride and 2 mM EDTA. The substituted DNA was analyzed by successive digestion with *N. crassa* endonuclease, snake venon phosphodiesterase DNAse, and *E. coli* alkaline phosphatase (H. Yamasaki et al, Cancer Res. 37:684-691, 1977). The mixture was eluted through DE-52 amino cellulose, and the nucleotides were analyzed by reverse phase HPLC using authentic 5-iodo-2'-deoxyuridine as a standard.

Example 18

Reaction of 5-Iodocytosine pBR322 DNA with Amines

Example of Reaction with 1,6-Diaminohexane

To the iodinated DNA from the previous reaction dialyzed into 1 ml 0.1 M sodium borate was added 116 mg (1 mmol) diaminohexane. The reaction mixture was flushed with argon and heated at 100° for 2 hours. The aminohexyl substituted DNA is exhaustively dialyzed into 0.01 M Tris HCl pH 7.5.

Reaction conditions for aminocaproic acid, bis(2-aminoethane)disulfide and 6-amino-α-methyl-D-manno (Example 5) are essentially identical.

Example 19

Coupling of Amino and Carboxy-Substituted Nucleic Acids to Proteins or Amines Using 1-Ethyl-3-diisopropyl-aminocarbodiimide (EDAC)

Example of Streptavidin Coupled DNA

To a solution containing amino- or -carboxy-end substituted DNA (Example 11) (50 μg) and 3H-labelled Streptavidin (50 μg) dissolved in 1 ml 0.01M NaCl pH 7.5 (HCl) was added 5 mg EDAC. The reaction was incubated 20 hours in the dark and DNA was precipitated by addition of 4 M $CaCl_2$ (0.03 ml). DNA was redissolved in 1 ml water and this procedure was repeated 2 more times to remove unbound protein. The protein-coupled DNA was affinity purified in an iminobiotin-sepharose affinity column (K. Hoffman et al, PNAS 77:4666 1980) and dialyzed against 10 mM NaCl.

Example 20

N-Hydroxy Succinimide Activation of Carboxyhexyl-Substituted DNA and Coupling to Proteins or Amines

Examples of Streptavidin Coupled DNA

Carboxy end substituted DNA (Example 19) (50 μg) was converted to the triethylammonium salt by shaking an aqueous solution with Dowex 50-WX ($Et_3N+$). The solution was lyophilized and the dried DNA was dissolved in anhydrous dimethyl formamide (0.5 ml) to which was added dicyclohexylcarbodiimide (10.3 mg, 0.05 mol) and N-Hydroxysuccinimide (5.8 mg 0.05 Mol). After incubating at room temperature for 20 hours the reaction was centrifugated and the supernatant dialyzed for 2 hours into 10 min NaCl. Streptavidin (50 μg) dissolved in 0.2 M borate, pH 9.5 (1 ml) was added to the N-hydroxysuccinimide activated DNA and the reaction was incubated 20 hours and dialyzed into 0.01M NaCl. The streptavidin coupled DNA was purified by $CaCl_2$ precipitation and iminobiotin affinity chromatography as previously described.

Example 21

Reaction of DNA with Glyoxal

DNA (1 μg) (DAM insert from plasmid pDK14) was dissolved in 0.025 M glyoxal (0.2 ml) and heated at 100° C. for 30 minutes in a sealed tube. The reaction was dialyzed against 10 mM NaCl. In order to assess degree of reaction on guanosine, a portion of the reaction was subjected to acid depurination by lowering the pH to 1.0 with HCl, and heating at 100° C. for 30 minutes. The depurinated DNA was removed by elution through DE-52 amino cellulose and the eluted purines analyzed by HPLC on reverse phase. Comparison of peak heights of adenosine, guanosine and glyoxal-guanosine adduct (R. Shapiro et al, Biochem 5:2799, 1966) revealed that 70% of the guanosines had been substituted.

Example 22

N-biotinyl-4-amino-acetophenone

To a solution of biotin-N-hydroxysuccinimide ester (50 μg, 0.014 mmol) dissolved in 20 ml dimethylformamide (DMF) was added 4-aminophenylacetophenone (4.35 g, 0.03 mol) dissolved in 50 ml DMF and 100 ml 0.1 M borate buffer pH 8.5. After reaction at room temperature for 20 hours, the solvent was removed by rotary evaporation. The residual oil was triturated first with 0.1 N HCl and then with 5% sodium bicarbonate. The product was crystallized from ethanol.

Example 23

Biotinyl (4-aminophenyl)glyoxal

Selenium dioxide (0.75 g, 7 mmol) was dissolved in 4 ml dioxane containing 0.15 ml water. To this was added dropwise a solution of N-biotinyl-4-amino acetophenone (1.9 g, 7 mmol) dissolved in 5 ml dioxane. The reaction was refluxed for 3.5 hours after which the mixture was filtered and concentrated under vacuum. The crude product as purified by silica gel chromatography.

Example 24

1,N-Biotinyl-1,6-hexanediamine

Biotin-N-hydroxysuccinimide ester (1.0 g, 2.9 mmol) dissolved iii dimethylformamide (5 μm) was added to a solution of diaminohexane (1.15 g, 10 mmol) in 0.1 M sodium borate (500 ml). After reacting at room temperature for 5 hours, the solution was rotary evaporated, redissolved in 10 ml water and chromatographed on Dowex® 50 wx (H+). The column was washed with 50% aqueous methanol and the fraction eluted with triethylamine dissolved in 50% aqueous methanol (0.3M) was collected. The evaporated residue was thoroughly triturated with ether and recrystallized from DMF/ether.

Example 25

To a solution of pyruvic acid (0.44 g, 5 mmol) cooled to 4° C., 20 ml anhydrous DMF was added isobutylchloroformated (0.64 g, 5 mmol) and tri-N-butylamine (1.43 g, 1.5 mmol). After 20 minutes at this temperature, an additional 1.4 g tri-N-butylamine was added and the mixture was added to a solution of 1,N-biotinyl-1,6-hexane diamine (Example 24) (0.34 g, 1 mmol) dissolved in 30 ml DMF and 30 ml 0.1 M sodium borate. After reacting at 4° C. for 1 hr. the mixture was allowed to stand at room temperature for an additional 20 hours and subsequently concentrated in vacuo. The mixture was purified by chromatography on silica gel and the product recrystallized from ethanol.

Example 26

Selenium dioxide (54 mg, 0.5 mmol) was dissolved in dioxane (0.5 ml) containing 25 μl water. A solution of $CH_3$—CO—CONH—$(CH_2)_6$—NH-Biotin (Example 25) (0.21 g 0.5 mmol) dissolved in 1 ml dioxane was added dropwise and the reaction was heated at 100° for 4 hours. The resultant precipitate was removed by centrifugation, washed with dioxane and the supernatant was concentrated in vacuo. The crude mixture was chromatographed on silica gel.

Example 27

Reaction of DNA with Biotinylated Glyoxal Derivatives

DNA (1 μg) as a triethylammonium salt was dissolved in 100 μl water. To this was added 100 μl of a solution of (N-biotinyl (4-aminophenyl)) glyoxal (0.05 M) or CHO—CO—CONH—$(CH_2)_6$—NH-Biotin (0.05M) in dimethylformamide. The mixture was heated at 100° C. for 30 minutes in a sealed tube and subsequently dialyzed against 0.01 M NaCl. Extent of reaction was determined by acid depurination and HPLC assay of purine nucleosides, as described previously.

Example 28

Bromination of pBR 322 DNA

To a solution of pBR 322 DNA (100 μg) dissolved in 0.5 M acetate buffer pH 5.5, was added bromine (5.5 μl, 0.1 mmol). The reaction was incubated at 60° for 30 hours and exhaustively dialyzed against 0.01 M NaCl.

Example 29

Reaction of Brominated pBR 322 DNA with Thiols

Example Reaction with Cysteamine and 3-Mercaptopropionic Acid

A solution of brominated pBR 322 DNA (500 μg) in 0.1 M borate pH 8.5 (1 ml) was incubated with either cysteamine or 3-mercaptopropionic acid (20 mg) for 20 hours at room temperature under an argon atmosphere. The resultant amine- or carboxy-substituted DNA was dialyzed against 0.01 M NaCl.

Example 30

Reaction of Brominated pBR322 DNA with Amines

Example of Reaction with 1,6-Diaminohexane

A solution of brominated pBR 322 DNA (100 μg) and 1 M of 1,6-diaminohexane (1 ml) were heated at 65° for 3 hours under an argon atmosphere. The resultant amine-substituted DNA was dialyzed against 0.1 M NaCl.

Example 31

Synthesis of a Protein Coupled to a Signal Generating Polynucleotide Example of IgG Coupled to Chemically Radio-Labeled DNA Fd DNA was end labelled with UMP using terminal transferase under conditions described in Example 11. The end labelled DNA was derivatized with 2,4,5-trichloroaniline (Example 1) and reacted with DCTA-SH under identical conditions to those described in Example 1a. The end labelled, DCTA derivatized DNA was oxidized with sodium periodate, reacted with cysteamine and reduced with sodium borohydride as described in Example 12. This was in turn reacted with bromoacetylated IgG (Example 14) using conditions described in Example 15.

Example 32

Use of Bacteriophage M13 as Bridging Entity

Using techniques of recombinant DNA technology, an asymmetric DNA sequence can be inserted in the replicative (double-stranded form) of a single-stranded phage such as M13. One strand of the insert will be deficient in guanine residues. As a result of this insertion, two single-stranded phages will be obtained in both polarities, one containing the (G−) strand, i.e., no guanylate residues of the asymmetric sequence, the other containing the sequence complementary to the G(−) sequence, to be called the G(+) sequence.

The G(+) phage is used as the vector (bridging entity) for carrying a DNA probe of interest such as, for example, herpes simplex virus I DNA sequences.

The G(−) phage (signalling entity) is chemically reacted with a guanosine specific reagent, such as a 1,2-dicarbonyl reagent. The G(−) insert in the G(−) phage would not be modified because it lacks guanylate residues.

A general protocol for the preparation of single-stranded M13 would be as follows:
1. M13 mp8 rf (replicative form, double-stranded), is grown. It is cut with Hinc II, which leaves blunt ends.
2. pd$(G-T)_5$ and pd$(A-C)_5$ are provided and hybridized to form a perfect double-strand. The ends must be perfectly matched. In order to obtain this condition it is necessary to use high $C_o t$ conditions for hybridization.
3. The hybrids are ligated in the presence of the restriction enzyme Rsa I. Rsa I recognizes the sequence GTAC, and hence will cut to leave blunt ends and proofread the ligation.
4. The ligation products are isolated. They are double-stranded poly d (G-T) poly d (A-C). (Any complementary, repeating, low complexity sequence can be used. The subsequent modification and chemistries must be adjusted accordingly.)
5. Alkaline phosphatase is used to remove 5' phosphates.

6. Polynucleotide kinase and $^{32}$P-ATP are used to replace 5' ends with $^{32}$P-phosphates.
7. The reaction mixture is run over 15-20% non-denaturing polyacrylamide gels to separate the different size fragments.
8. The fragments are located on gels by autoradiography.
9. The desired size bands are eluted out of the gel by cutting, mashing and then extracting the gel with high salt buffer. Fragments having 50-100 bp or larger are preferred:
10. DMA is concentrated by any of a number of possible techniques, such as ethanol precipitation, spermine precipitation, lyophilization, or the like.
11. The fragments are ready to be cloned into Hinc II-cut M13.

Using a standard cloning technique, the following sequence is performed:
   a. Fragments are ligated into M13;
   b. Cells (for example *E. coli* JM103) are transformed with the M13;
   c. Transformed cells are plated; and
   d. Recombinants are selected.

12. There are two possible routes for selection of recombinants:
   a. If a known size class has been inserted, plaques will be picked and sequenced to check for the presence of insert.
   b. An alternative procedure is to shotgun all the sequences made in step 4 into M13. This protocol requires that many more clones be picked and then checked by sequencing.
13. Once a suitable clone has been obtained (M13 with the appropriate size sequence), the strand that gives GTGT, etc., in the single-strand replicating form will be selected. This clone is then used for further genetic engineering by inserting sequences from a variety of pathogens into the replicating form.
14. The strand that gives ACAC etc. in the replicating form is cloned in mass culture and chemically modified with a reporter (signal generation portion) that is specific for G's. Thus the G(−) phage is exhaustively reacted with the bifunctional reagent p-azidophenyl glyoxal (APG). The dicarbonyl moiety of APG reacts only with guanosine residues in single-stranded portions of the DNA. The insert lacking guanosine is not affected by this treatment.
15. The (G+) and derivatized (G−) DNAs are mixed in equimolar concentration and allowed to hybridize to target DNAs and to each other. Visualization of the hybrids is by standard signal reporting techniques.

Having now fully described this invention, it will be understood by those of ordinary skill in the art that the same can be subject to a wide range of modifications, to generate equivalent systems and processes, without affecting the spirit or scope of the invention or of any embodiment described therein.

What is claimed as new and intended to be covered by Letters Patent of the United States is:

1. A polynucleotide sequence covalently attached to a monoclonal antibody.
2. A polynucleotide sequence covalently attached to a lectin.
3. A polynucleotide sequence covalently attached to a hormone receptor.
4. A polynucleotide sequence covalently attached to a hormone.
5. A circular DNA molecule covalently attached to a non-radiolabeled signal generating moiety that comprises an enzyme.
6. A circular DNA molecule comprising a polynucleotide that encodes part or all of a gene, wherein the DNA molecule is covalently attached to a non-radiolabeled signal generating moiety that comprises biotin.
7. A circular DNA molecule comprising a polynucleotide that encodes part or all of a gene, wherein the DNA molecule is covalently attached to a non-radiolabeled signal generating moiety that comprises an antibody.
8. A circular DNA molecule comprising a polynucleotide that encodes part or all of a gene, wherein the DNA molecule is covalently attached to a non-radiolabeled signal generating moiety that comprises a fluorogenic compound.

\* \* \* \* \*